United States Patent
Cho et al.

(10) Patent No.: US 11,975,171 B2
(45) Date of Patent: May 7, 2024

(54) ON-DEMAND DOSE CONTROLLABLE DRUG RELEASING DEVICES AND METHODS

(71) Applicant: University of Pittsburgh—Of the Commonwealth System of Higher Education, Pittsburgh, PA (US)

(72) Inventors: Sung Kwon Cho, Pittsburgh, PA (US); Fang-Wei Liu, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 643 days.

(21) Appl. No.: 17/151,173

(22) Filed: Jan. 17, 2021

(65) Prior Publication Data
US 2021/0220553 A1    Jul. 22, 2021

Related U.S. Application Data

(60) Provisional application No. 62/962,560, filed on Jan. 17, 2020.

(51) Int. Cl.
*A61M 5/142* (2006.01)
*G16H 20/17* (2018.01)

(52) U.S. Cl.
CPC ........ *A61M 5/14276* (2013.01); *G16H 20/17* (2018.01); *A61M 2205/3507* (2013.01); *A61M 2205/3553* (2013.01)

(58) Field of Classification Search
CPC .............................................. A61M 5/14276
See application file for complete search history.

(56) References Cited

U.S. PATENT DOCUMENTS

| 4,620,965 A | 11/1986 | Fukusawa |
| 4,770,675 A | 9/1988 | Kurzweg |
| 4,770,786 A | 9/1988 | Manabe |
| 7,981,368 B2 | 7/2011 | Laugharn, Jr. |
| 8,734,382 B2 | 5/2014 | Frankowski |
| 2003/0175947 A1 | 9/2003 | Liu |
| 2004/0157093 A1 | 8/2004 | Mardilovich |

(Continued)

FOREIGN PATENT DOCUMENTS

WO    WO2017127777    7/2017

OTHER PUBLICATIONS

Ryu et al. Micropumping by an Acoustically Excited Oscillating Bubble for Automated Implantable Microfluidic Devices. JALA. Jun. 2010, pp. 163-171 (Year: 2010).*

(Continued)

*Primary Examiner* — Jenna Zhang
(74) *Attorney, Agent, or Firm* — BARTONY & ASSOCIATES, LLC (57) ABSTRACT

A system includes a delivery system a tube having a first open end and a second closed end, wherein the inner wall of the tube exhibits or includes surface roughness, a first liquid volume including a first liquid within the tube, and a first gas volume within the tube adjacent the first open end and separating the first liquid volume from a surrounding environment. The system further include a drive system, remote from the delivery system, which is configured to transmit a signal to controllably oscillate the first gas volume and one or more other gas volumes within the tube.

26 Claims, 5 Drawing Sheets

(56) References Cited

U.S. PATENT DOCUMENTS

| | | | |
|---|---|---|---|
| 2008/0142441 A1 | 6/2008 | Pashley | |
| 2008/0314820 A1 | 12/2008 | Prulhiere | |
| 2015/0251141 A1 | 9/2015 | Mourad | |
| 2018/0071505 A1* | 3/2018 | Lo | A61K 9/0009 |
| 2019/0201615 A1* | 7/2019 | You | A61M 37/0015 |

OTHER PUBLICATIONS

Wang et al. Dynamics of underwater gas bubbles impact on a ratchet with gradient inclination. Applied Surface Science. 475 (2019), pp. 598-605 (Year: 2019).*

Hassan, Shabir et al., Microfluidic technologies for local drug delivery, Chapter 10, William Andrew Publishing, 2019, pp. 281-305.

Sanjay, S. T., et al., Recent advances of controlled drug delivery using microfluidic platforms, Advanced Drug Delivery Reviews 128 (2018) 3-28.

Jang, D et al., Targeted drug delivery technology using untethered microrobots: a review, J. Micromech. Microeng., vol. 29, 2019, pp. 1-25.

Meng, E. and Hoang, T., Micro- and nano-fabricated implantable drug delivery systems, Ther. Deliv., vol. 3, pp. 1-18, 2012.

Riahi, R et al., , Microfluidics for advanced drug delivery systems, Curr. Opin. Chem. Eng., vol. 7, pp. 1-21, 2015.

Lo, R., et al., A passive MEMS drug delivery pump for treatment of ocular diseases, Biomed Microdevices, vol. 11, p. 659-970, 2009.

Chung, A. J. et al., A robust, electrochemically driven microwell drug delivery system for controlled vasopressin release, Biomed Microdevices, vol. 11, p. 861-867, 2009.

Elman, M., et al., An implantable MEMS drug delivery device for rapid delivery in ambulatory emergency care, Biomed Microdevices, vol. 11, p. 625-631, 2009.

Ali, M. et al., A pH-Tunable nanofluidic diode with a broad range of rectifying properties, ACS Nano, vol. 3, pp. 603-608, 2009.

Pirmoradi, F. N. et al., "A magnetically controlled MEMS device for drug delivery: design, fabrication, and testing," Lab Chip, vol. 17, pp. 3072-2080, 2011.

Jeong, J., et al., Target drug delivery technology (carrying, releasing, penetrating) using acoustic bubbles embedded In an electromagnetically driven microrobot, presented at the IEEE Micro Electro Mechanical Systems, Belfast, Northern Ireland, UK, 2018.

Kamaly, N., et al., Degradable Controlled-Release Polymers and Polymeric Nanoparticles: Mechanisms of Controlling Drug Release, Chem. Rev., 2016, 116, 4, pp. 2602-2663.

Liu, Fang-Wei et al., . 3-D Micro Swimming Drone With Maneuverability, MEMS 2019, Seoul, Korea, pp. 10-13.

Wang, Xiang et al., Dynamics of underwater gas bubbles impact on a ratchet with gradient inclination, Applied Surface Science 475 (2019) 598-605.

Ryu, Kyungjoo et al., Micropumping by an Acoustically Excited Oscillating Bubble for Automated Implantable Microfluidic Devices, JALA, Jun. 2010, pp. 163-171.

Dolgin, E. Artificial inspiration, Nature, vol. 489, 2012, pp. S12-S14.

Potkay, J. A. The promise of microfluidic artificial lungs, Lab Chip, vol. 14, pp. 4122-4138, 2014.

Hattler, B.G. et al., A respiratory gas exchange catheter: In vitro and in vivo tests in large animals, J. Thorac. Cardiovasc. Surg., 2002, 520-530.

Hoganson, D. M. et al., Lung assist device technology with physiologic blood flow developed on a tissue engineered scaffold platform, Lab Chip, vol. 11, pp. 700-707, 2011.

Potkay, J. A. et al., Bio-inspired, efficient, artificial lung employing air as the ventilating gas, Lab Chip, vol. 11, pp. 2901-2909, 2011.

Kniazeva, T., et al., Performance and scaling effects in a multilayer microfluidic extracorporeal lung oxygenation device, Lab Chip, vol. 12, pp. 1686-1695, 2012.

Rochow, N. et al., An integrated array of microfluidic oxygenators as a neonatal lung assist devices: In vitro characterization and in vivo demonstration, Artificial Organs, vol. 38, pp. 856-866, 2014.

Robb, W.L. Thin Silicon membranes-Their permeation properties and some applications, Ann. N. Y. Acad. Sci., vol. 146, pp. 119-137, 1968.

B. Chang, et al., Low-height sharp edged patterns for capillary self-alignment assisted hybrid microassembly, J Micro-Bio Robot, 2014, 9:1-10.

Feng, J. et al., Micro propulsion in liquid by oscillating bubbles, presented at the 2013 IEEE 26th International Conference on Micro Electro Mechanical System (MEMS), Taipei, 2013, 63-66.

Feng, J. et al., Micropropulsion by an acoustic bubble for navigating microfluidic spaces, Lab Chip, vol. 15, pp. 1554-1562, 2015.

Feng, J. et al., Two-Dimensionally Steering Microswimmer Propelled by Oscillating Bubbles, presented at the 2014 IEEE 23rd International Conference on Micro Electro Mechanical Systems (MEMS), San Francisco, 2014, 188-191.

* cited by examiner

ON-DEMAND DOSE CONTROLLABLE DRUG RELEASING DEVICES AND METHODS

CROSS-REFERENCE TO RELATED APPLICATIONS

This application claims benefit of U.S. Provisional Patent Application Ser. No. 62/962,560, filed Jan. 17, 2020, the disclosure of which is incorporated herein by reference.

GOVERNMENTAL INTEREST

This invention was made with government support under grant no. 1637815 awarded by the National Science Foundation. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Drug delivery aims to administer a biologically active or pharmaceutically active compound or formulation (for example, including a drug) to one or more region of interest or target location in the body (for example, to one or more pathological sites or a specific organ or tissue). The pharmaceutical formulation may function, for example, as a diagnostic tool or as a therapy. Traditional pharmaceutical delivery routes include oral administration, inhalation, hypodermic or transdermal injection. However, several drawbacks exist in such routes. In that regard, a drug is usually released at the location distant from the target location, resulting in loss and degradation. Higher dosages or concentrations than required at the target location are thus used for the treatment and may cause toxicity to healthy tissue. Ideally, a drug delivery system for therapy is capable of maintaining drug levels within a therapeutic window and adequate fluctuation over a desired period to maximize the therapeutic efficacy and minimize systemic toxicity. To address such issues, there have been attempts to develop localized drug delivery systems to release drugs in the target location with a desired profile via a drug loaded carrier or implantable microsystem. Such systems may be designed to store and release drug by either passive or active methods. Passive release is usually based on diffusion by drug-infused porous material or drug-permeable membrane, which provides a long and continuous release with less fluctuation. On the other hand, certain therapies may require a pulsatile (or other) release profile that, for example, mimics the body's natural function (for example, insulin delivery or hormone-based drug). Pulsatile and other release profiles may require active control. Microfluidic systems may provide advantages for active drug release as a result of their ability to precisely manipulate fluids in small quantity. However, difficulties persist in controlling the delivery of fluids from implanted microfluidic systems.

SUMMARY

In one aspect, a system hereof includes a delivery system including a tube having a first open end and a second closed end, wherein the inner wall of the tube exhibits or includes surface roughness, a first liquid volume including a first liquid within the tube, and a first gas volume within the tube adjacent the first open end and separating the first liquid volume from a surrounding environment. The system further includes a drive system, remote from the delivery system, which is configured to transmit a signal to controllably oscillate the first gas volume. In a number of embodiments, the delivery system is an implantable system and the drive system is ex vivo. In a number of embodiments, the inner wall is hydrophobic. The drive system may, for example, be configured to transmit the signal to controllably oscillate the first gas volume so that mass is transferred across a length of the tube occupied by the first gas volume from the first liquid volume to the surrounding environment during oscillation of the first gas volume. The signal from the drive system may, for example, be a pressure wave or acoustic signal.

In a number of embodiments, the tube includes a plurality of axially spaced flanges extending radially inward (to provide surface roughness or texture). The plurality of axially spaced flanges may, for example, form a ratchet-like surface.

The delivery system may further include a second gas volume positioned within the tube so that the first liquid volume is positioned between the first gas volume and the second gas volume. In such embodiments, the signal from the drive system is further configured or adapted to controllably oscillate the second gas volume. In a number of embodiments, the delivery system further includes at least a second liquid volume including a second liquid within the tube adjacent the second gas volume on a side thereof opposite to a side adjacent the first liquid volume and a third gas volume adjacent the second liquid volume on a side thereof opposite the side adjacent the second gas volume. In such embodiments, the signal from the drive system is further configured or adapted to controllably oscillate the second gas volume. In a number of embodiments, the composition of the second liquid volume is different from the composition of the first liquid volume.

The drive system may, for example, be controlled to control/transmit the signal to be within a determined range of amplitude and a determined range of frequency. In a number of embodiments, a duty cycle of the drive system (during an activation cycle) is controlled to control oscillation of the first gas volume and the second gas volume. The drive system may, for example, include a piezo actuator or a pressure wave generator.

In a number of embodiments, the tube has an average inner diameter no greater than 3 cm, no greater than 5 mm, or no greater than 500 µm. The average inner diameter is defined as the diameter of a circle passing through the middle point of the height of the roughness or texture of the tube. In a number of embodiments, the tube has a length in the range of 10 µm to 3 cm, in the range of 10 µm to 2 mm, in the range of 100 µm to 1 mm, or in the range of 10 µm to 100 µm.

In another aspect, a method of mass exchange between a delivery system and an environment including a liquid includes placing the delivery system in the environment. The delivery system includes a tube having a first open end and a second closed end, wherein an inner wall of the tube exhibits or has surface roughness, a first liquid volume including a first liquid within the tube, and a first gas volume within the tube adjacent the first open end and separating the first liquid volume from the environment. The method further includes transmitting a signal from a position remote form the delivery system which is configured or adapted to controllably oscillate the first gas volume. As described above, the inner wall of the tube may, for example, be hydrophobic. The environment may, for example, be an in vivo environment. In such embodiments, the delivery system may be an implantable system, the liquid in the environment may be a bodily fluid, and the position remote from the delivery system may be an ex vivo position. In a number of embodiments, the drive system is configured to transmit the signal to controllably oscillate the first gas volume so that mass is transferred across a length of the tube occupied by the first gas volume from the first liquid volume to the environment surrounding the delivery system during oscillation of the first gas volume. The signal may, for example, be generated via an external drive system comprising a piezo actuator or a pressure wave generator.

In a number of embodiments, the method further includes controlling the signal to be within a determined range of amplitude and a determined range of frequency. In a number of embodiments, a duty cycle of the drive system (curing an activation cycle) is controlled to control oscillation of the first gas volume and the second gas volume. The drive system may, for example, include a piezo actuator or a pressure wave generator.

The method and delivery system used therein may be further characterized as described above and elsewhere herein. For example, in a number of embodiments, the tube includes a plurality of axially spaced flanges extending radially inward (to provide surface roughness or texture). The plurality of axially spaced flanges may, for example, form a ratchet-like surface.

The delivery system may further include a second gas volume positioned within the tube so that the first liquid volume is positioned between the first gas volume and the second gas volume. In such embodiments, the signal from the drive system is further configured or adapted to controllably oscillate the second gas volume. In a number of embodiments, the delivery system further includes at least a second liquid volume including a second liquid within the tube adjacent the second gas volume on a side thereof opposite to a side adjacent the first liquid volume and a third gas volume adjacent the second liquid volume on a side thereof opposite the side adjacent the second gas volume. In such embodiments, the signal from the drive system is further configured or adapted to controllably oscillate the second gas volume. In a number of embodiments, the composition of the second liquid volume is different from the composition of the first liquid volume.

In a number of embodiments, the tube has an average inner diameter no greater than 3 cm, no greater than 5 mm, or no greater than 500 µm. In a number of embodiments, the tube has a length in the range of 10 µm to 3 cm, in the range of 10 µm to 2 mm, in the range of 100 lam to 1 mm, or in the range of 10 µm to 100 µm.

The devices, systems, and methods hereof, along with the attributes and attendant advantages thereof, will best be appreciated and understood in view of the following detailed description taken in conjunction with the accompanying drawings.

DETAILED DESCRIPTION

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a microtube" includes a plurality of such microtubes and equivalents thereof known to those skilled in the art, and so forth, and reference to "the microtube" is a reference to one or more such microtubes and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but are not limited to, hardware, firmware, software, or combinations of each to perform a function(s) or an action(s). For example, based on a desired feature or need, a circuit may include a software-controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software-controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The terms "controller" or "control system" as used herein includes, but is not limited to, any circuit or device that coordinates and controls the operation of one or more input and/or output devices. A controller may, for example, include a device having one or more processors, microprocessors, or central processing units capable of being programmed to perform functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiments, devices, systems, and method hereof provide for micro-scale mass transport in a liquid phase with a controllable release profile which may be remotely controlled by remote activation (for example, via acoustic or pressure wave excitation). In general, one or more volumes of liquid (sometimes referred to herein as liquid droplets) within the tube are used as a releasing agent or as a liquid drug. In a number of embodiments, a liquid droplet (including a first liquid or first liquid composition) is contained or trapped within a tube or conduit (for example, a microtube or micro-conduit) by adjacent volumes of gas (sometimes referred to herein as gaseous or gas bubbles). Tubes or conduits hereof need not be of circular cross section. Such tubes or conduits may, for example, be square, rectangular, triangular, or of other cross-sectional shapes wherein the inner wall forms a boundary enclosing or encompassing the fluid within. One gas volume or gas bubble is positioned on each side of the liquid droplet. Activation via a remote energy source (for example, excitation via an induced acoustic or pressure wave field) induces oscillation/resonance in the gaseous bubbles. Without limitation to any mechanism, oscillation of the first gas bubble, which is closest to the forward, open end of the microtube, causes segregation of the liquid droplet into smaller droplets which are transferred/delivered out of the microtube via the open end thereof. Liquid from the surrounding environment in which the microtube is positioned/implanted is segregated and transferred/delivered in the same manner into the microtube at a similar rate. Once again, without limitation to any mechanism, the second gas bubble, which is closest to the rearward, closed end of the microtube (adjacent the rearward side of the liquid droplet) enhances mixing of incoming liquid mass from the surrounding environment with the liquid within the droplet, thereby promoting the efficiency of mass transport.

Surface roughness or texture on the interior or inner wall of the tube or microtube, which is adjacent the liquid droplet(s) and gaseous bubble(s), can be used to improve or optimize mass transfer from the liquid droplet(s) and control of such mass transfer. Surface roughness or texture can be designed or selected to achieve a predetermined mass transfer profile over time. In a number of embodiments, a controlled surface texture or roughness is created by forming spaced members, flanges or teeth which extend radially from the internal wall of the microtube. In a number of embodiments, the flanges or teeth are spaced regularly or periodically. Such flanges or teeth may, for example, form a ratchet-like structure or rachet track on the inner wall of microtube. Mass transport from (and/or within) the microtube is also dependent upon the energy input thereto (for example, on the amplitude and the actuation/activation frequency), which is proportional to the activation or excitation period. It is thus possible to achieve predetermined, arbitrary release profiles (for example, for different therapeutic or diagnostic purposes). The micro-mass transport devices, systems and methods hereof thus provide a new mechanism for in vivo, on-demand, dose controllable delivery of pharmaceuticals. Although the devices, systems and methods hereof are particularly well suited for the delivery of pharmaceuticals, they can be used in any liquid-containing environment to achieve mass exchange. Virtually any liquid composition may be delivered via the devices, systems, and method hereof. Mass transport characteristics of such liquid compositions will depend on the liquid properties (including, for example, viscosity, density, wettability, etc.). Such mass transport characteristics are readily characterizable via well-known engineering principles and via experimental studies described herein. Solids suspended in liquid compositions hereof may also be transported/delivers as illustrated by the experimental results discussed in connection with FIG. 7C below.

Figures 1A, 1B, 1C:
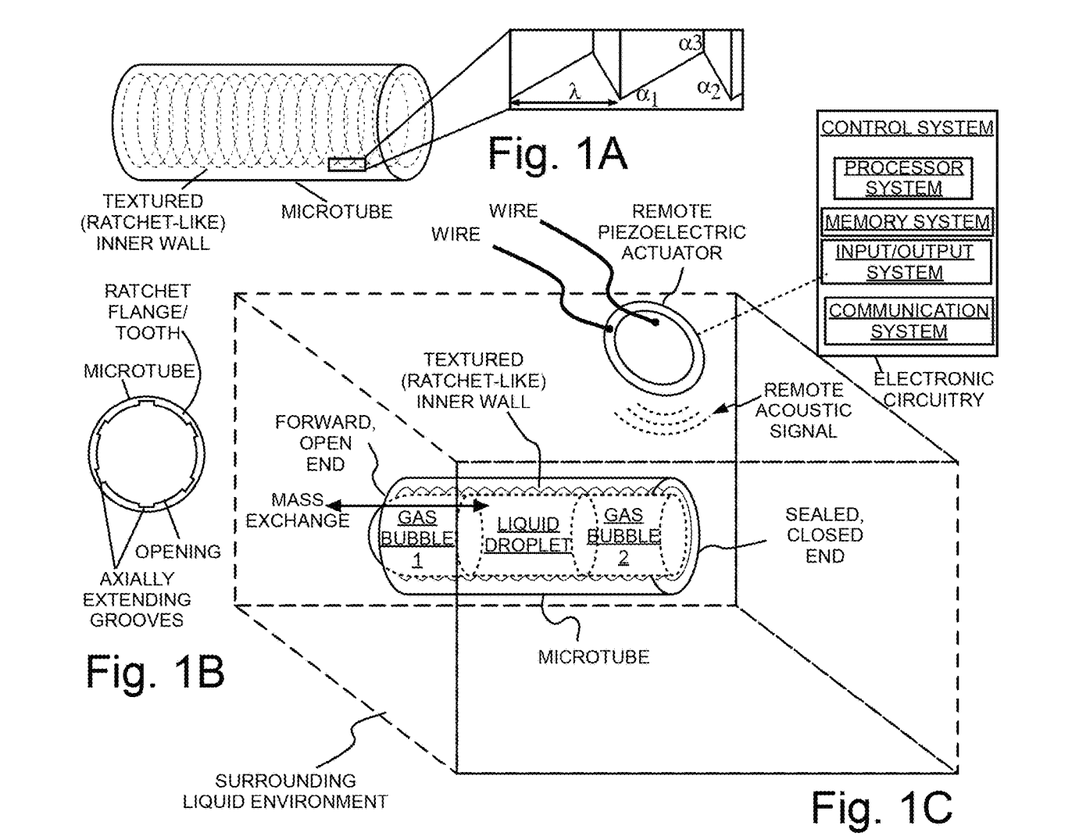
FIG. 1A illustrates schematically an embodiment of a microtube-based delivery system hereof including a ratchet-like textured inner wall.
FIG. 1B illustrates schematically a front view of the microtube of FIG. 1A illustrating a plurality of axially extending grooves formed in the ratchet-like flanges or teeth of the inner wall of the microtube.
FIG. 1C illustrates a schematic or idealized representation of micro-mass transport through the micro-conduit or microtube of FIG. 1A.

FIGS. 1A through 1C illustrate an embodiment of a microtubular implantable device or system hereof and the micro-mass transport of a first liquid from a liquid droplet through such an implantable device or system. In the embodiment of FIGS. 1A through 1C, an implantable tube or microtube includes a ratchet-like interior wall texture, one open end, and one sealed end. A liquid volume/droplet is trapped between the open end and the sealed end. In that regard, the liquid droplet (including the first liquid) is neighbored by two gas (for example, air) volumes/bubbles. In the illustrated embodiment, a remote or external drive delivers energy to the microtube. The drive may, for example, be a piezoelectric actuator (for example, a piezodisk as illustrated in FIG. 1B) or other actuator which generates acoustic/pressure waves and excites oscillation of the gaseous bubble(s) within the microtube. Liquid mass from the droplet is delivered to the surrounding liquid-containing environment and liquid mass from the surrounding environment is transported into the droplet at similar rate. Either continuous or pulsatile release/delivery of mass from the implantable devices and systems hereof may be achieved.

The dosage-programmable, remotely activatable devices, systems and methods hereof use a tube or microtube as a pharmaceutical/drug reservoir. In a number of representative studies, mass transport occurs between a liquid (water) droplet (which may be representative of one or more pharmaceuticals or other compositions to be delivered) and a liquid environment (representative of, for example, an in vivo region of interest for implantation) in which the microtube was submerged. The liquid droplet was first placed in the middle of the microtube. So the gaseous bubble in the sealed end forms. When the microtube with droplet therein was submerged in the representative liquid environment (that is, an environment including a liquid for mass exchange with one or more liquid droplets within the microtube), the gaseous bubble in the open end automatically formed inside the microtube. As a result, one on each side of the droplet (see, for example, FIG. 1B).

Absent external acoustic excitation, forward, gaseous bubble 1 (near the tube opening) acts as a membrane that isolates the liquid droplet from the surrounding liquid environment. When a remote or externally generated acoustic wave is applied to the microtube, forward gas bubble 1 oscillates and functions contemporaneously in a manner similar to the combined function of a valve and a pump. Externally generated acoustic waves are applied to the microtube in a controlled manner such that bubble 1 is relatively stable during one or more cycles of activation of the acoustic waves. In general, the volume and the position of the center of mass of bubble 1 (and other gas volumes or gas bubbles within a tube hereof) do not change significantly. In that regard, the volume of such gas bubbles does not change by more than 30%, more than 20%, or more than 10% in a number of embodiment hereof. Moreover, the center of mass of bubbles hereof does not change significantly during one or more cycles of activation. In that regards, the position of the center of mass does not change by more than 10% in a number of embodiments hereof. Gas bubble 1 is controllably oscillated so that mass is transferred across a length of the tube occupied by gas bubble 1 from the first liquid volume to the surrounding environment during oscillation gas bubble 1 without destruction of gas bubble 1 and without significant change in the position or the volume thereof. Gas bubble 1 functions contemporaneously in a manner similar to the combined function of a valve and a pump over a period of time (for example, over multiple activation cycles) to achieve a determined mass transport profile.

As described above, at a certain frequency or range of frequencies of an externally generated acoustic wave, the oscillation of forward, gas bubble 1 segregates the liquid droplet into smaller droplets and transports the smaller droplets from the position of the liquid droplet to the surrounding liquid environment. In general, the center of mass of the liquid droplet does not significantly translate or change (for example, more than 10%) within microtube during mass transport. Similarly, liquid from the surrounding liquid environment is segregated into small droplets via the oscillation of forward, gas bubble 1. The liquid droplets from the surrounding liquid environment are transported into the microtube. The roughness or texture (for example, ratchet-like structure) on the microtube inner wall enhances the mobility/mass transport of segregated liquid droplets. As also described above, rearward, gas bubble 2 (near the sealed end of the microtube) also oscillates and promotes mixing within the liquid droplet to achieve efficient and significant mass transport.

Once again, surface texture or roughness can be used to improve or optimize mass transport/exchange in the devices, systems, and methods hereof. In general, surface texture or roughness is defined (and may be quantified) by deviations in the direction of the normal vector of a real surface from its ideal form. Without limitation to any mechanism, it is believed that surface texture or roughness creates point contacts for liquid droplets of the implantable devices and systems hereof with generally radially inward projections/roughness of the interior wall of the tube or microtube.

Surface texture or roughness decreases the amplitude of the acoustic signal required to oscillate the forward gas bubble 1 in a manner to cause the liquid from the microtube to be transported/delivered to the surrounding liquid environment (and/or to cause transport of liquid from the surrounding liquid environment into the microtube). Once again, the tube or microtube may, for example, include a plurality of axially spaced flanges extending radially inward. Such flanges may, for example, be positioned at a defined periodicity. In a number of embodiments, the plurality of flanges forms a ratchet or ratchet-like surface texture or roughness. Surface roughness or texture of tubes hereof may be non-periodic or random but, periodic structure may provide for increased predictability in mass transport. Directionality and/or other characteristics of asymmetric, ratchet-like flanges or teeth may be used as parameters to control mass transfer. In a number of embodiments, such flanges and/or other deviations/projections extend radially inward (or have a height h) a distance greater than or equal to 7.5% of the average diameter of the inner wall of the tube.

The devices, systems and methods hereof may be used not only to deliver mass from a liquid droplet within the microtube to an outside environment but also to achieve mixing of mass from different droplets inside the microtube. By placing two liquid droplets at spaced positions within the microtube, oscillation of a gaseous bubble positioned between and adjacent to the liquid droplets can achieve generally uniform mixing between the two droplets. Relatively complex manipulation of liquid volumes/masses and mass exchange thereof with the surrounding liquid environment may be achieved at micro-scale.

The rate of oscillating-bubble-induced mass transfer is controllable via control of the duty cycle of the externally generated acoustic wave. Since the release rate and amount is controllable, arbitrary release profiles can be predetermined and achieved. Control may, for example, be achieved via a control system which is a component of electronic circuitry of a system hereof. Those skilled in the art will appreciate that electronic circuitry, including, for example, a processor system in operative connection with a memory system, may include software including one or more algorithms stored in memory system and executable by processor system to operate, at least in part, as a control system or controller to independently control the externally generated acoustic wave. As known in the computer arts, an input/output system may be in operative connection with the processor system and the memory system to, for example, acquire data input from, for example, the drive system, from a sensor system (not shown) and/or from one or more users, as well as to output data/information. One or more sensors such as a color intensity sensor, a pH sensor, a conductivity sensor, etc. may, for example, be used to measure how much mass transport occurs between the liquid droplet withing a microtube hereof and a surrounding liquid-containing environment. Data from such a sensor may, for example, be used to characterize the mass transport and/or to effect feedback control of the drive system. Although software algorithms hereof may be executed via the electronic circuitry, one skilled in the art appreciates that such algorithms may, for example, be stored and executed separately (for example, via a separate computer) or that storage of such algorithms and execution thereof may be distributed over a number of devices or systems. A communication system may, for example, be provided to effect communication between the electronic circuitry and one or more remote systems.

Figure 2:
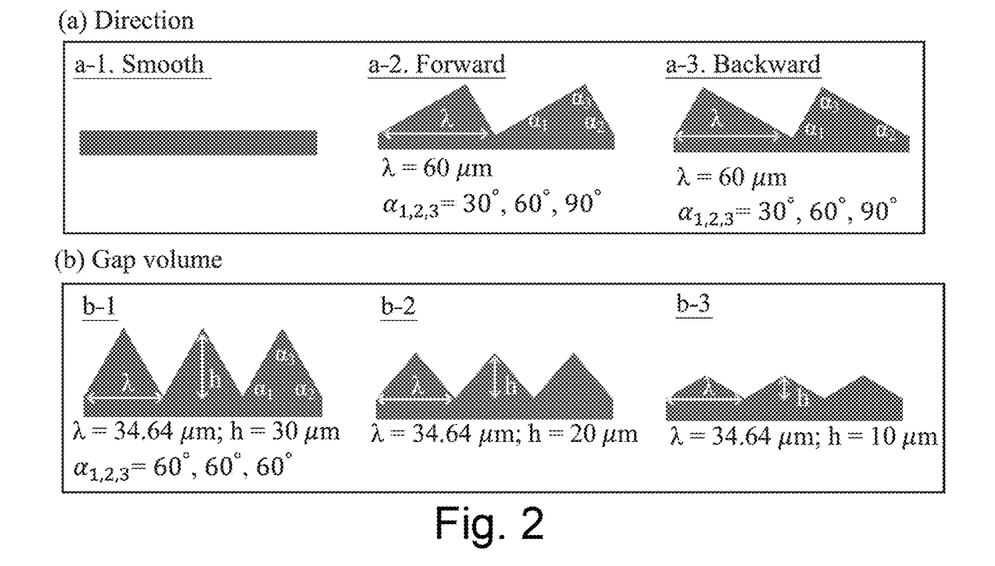
FIG. 2 illustrates the design of a number of ratchet-like geometries for interior or inner walls of conduits or tubes hereof wherein panel (a) illustrates radially extending asymmetric triangular flanges or teeth of opposite direction and panel (b) illustrates symmetric triangular flanges or teeth having different cross-sectional areas.

In a number of representative embodiments, representative studied microtubes had an average diameter of approximately 400 μm and were approximately 2000 μm in length with one end opened. The other end was closed or sealed as described above. As illustrated in FIG. 2, microtubes having a smooth or flat inner wall/surface (inner wall design a-1) as well as microtubes having a rough or textured inner wall/surface (for example, formed with a ratchet-like or triangular (in cross-section) pattern; see inner wall designs a-2, a-3, b-1, b-2 and b-3) were studied. In a number of studied microtubes with a ratchet-like inner wall design, a plurality (for example, six) grooves having a width of approximately 5 μm were embedded or formed in the textured/ratchet pattern along the axial direction to assist the communication of gas between the two bubbles to maintain the bubble size and to provide for smoother mass transport. In the case of tubes of non-circular cross section, angled corners (for example, of a tube of polygonal cross section) may function in a manner similar to the grooves described above. A first group of ratchet-like inner wall designs (inner wall designs a-2 and 2-3) had a triangular shape with a base having period $\lambda$ of 60 μm and a top angle $\alpha_3$ of 90°. Two different directions of ratchet flanges or teeth were designed to study the impact ratchet geometry on mass transport. Interior wall design a-2 is referred to herein as a forward ratchet design and interior wall design a-3 is referred to herein as a backward ratchet design. Such ratchet-like interior wall designs have a leading ratchet angle $\alpha_1$, pointing to the opening end, at 30° and 60°, respectively, and a receding angle $\alpha_2$, pointing to the sealed end, at 60° and 30°, respectively, as shown in panel (a) of FIG. 2. A second group of ratchet-like interior wall designs b-1, b-2 and b-3 include a symmetric triangular shape having different cross-sectional area as shown in panel b of FIG. 2.

Figure 3:
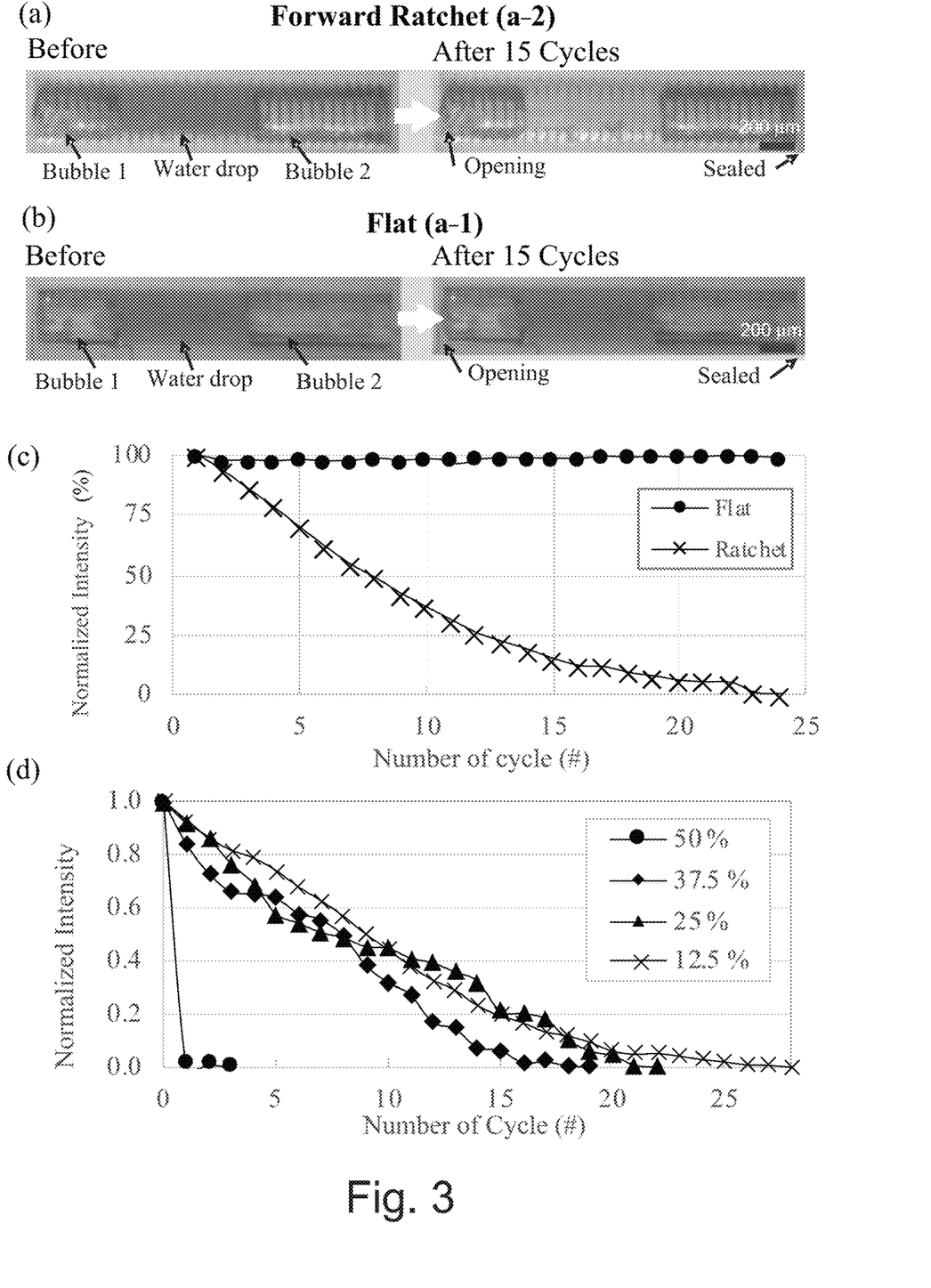
FIG. 3 illustrates studies of embodiments of microtubes hereof, wherein: panel (a) illustrates a forward ratchet inner wall design a-2; panel (b) illustrates a smooth or flat inner wall design a-1, wherein the photographs of panels (a) and (b) were taken in inactivated state before any activation and after 15 cycles of activation and all scale bars are 200 µm; panel (c) illustrates quantification of mass transport in a comparison of the forward-ratchet wall microtube (inner wall design a-2) and the flat wall microtube (inner wall design (a-1) for 24 activation cycles; and panel (d) illustrates quantification of mass transport in the forward-ratchet wall microtube (inner wall design a-2) under an activation signal with duty cycles of %, 37.5%, 25% and 12.5%.

Photographs of fabricated microtubes are displayed in panels (a) and (b) of FIG. 3 wherein portions at the rearward and forward ends of the microtube contain gas/air bubbles 1 and 2, respectively, and the portion in the middle initially contains a blue-dyed water droplet. The studied microtubes were immersed in undyed water as a surrounding liquid environment. In a number of studies, an excitation signal was given at 2.4 kHz, 5.5 V, and an activation period of 2 seconds with 50% duty cycle (that is, 1-second activation and 1-second inactivation in each cycle). Duty cycle is the ratio of ACTIVE or ON time/(ON time+REST time). ON time+REST time is the activation period or cycle.

The photographs of panels (a) and (b) of FIG. 3 were taken (i) before any actuation of the piezo-disk and (ii) during a period of inactivation after 15 effective activation cycles. The liquid droplet inside the microtube with a ratchet-like inner wall design a-2 has a significant fade in color with negligible volume change (see the right side of panel (a) of FIG. 3). On the other hand, the liquid droplet within a microtube having the same dimensions but with a flat (non-textured) inner wall (that is, inner wall design a-1) had no observable change in color under the same excitation input (see panel (b) of FIG. 3). The results indicate that the content of the original droplet (blue-dyed water) is transported or delivered to the clear, undyed water surrounding the microtube including inner wall design a-2, while a similar amount of the clear, undyed water from the surrounding water environment was transported from the surrounding water environment to the location of the liquid droplet inside the microtube. However, little if any mass transfer occurred between the liquid droplet and the surrounding water environment in the studies of the microtube including smooth or flat inner wall design a-1. The studies represented by the example of panels (a) and (b) demonstrate that surface texture or roughness such as the ratchet-like structure of inner wall design a-2 assists in achieving significant mass transport between the liquid droplet within the microtube and the surrounding liquid environment.

Mass transport rate between the liquid droplet within the microtubes and the surrounding liquid environment may, for example, be quantified by measuring the change in dye intensity (color) of the droplet after each cycle. ImageJ software (image analysis software available from the National Institutes of Health of the Unites States of America and the Laboratory for Optical and Computational Instrumentation of the University of Wisconsin) was used to determine the intensity of the droplet color. The normalized intensity is defined by (measured intensity of droplet—intensity of droplet without dye)/(initial intensity of droplet with dye—intensity of water droplet without dye). The axis label of FIG. 3(d) is "Normalized Intensity (no unit)". The color intensity of the liquid droplet is linearly dependent upon the concentration of dye in the liquid droplet. The measured intensities of the liquid droplet after each activation cycle of the microtube including ratchet-like inner wall design a-2 and the microtube including a flat inner wall design a-1 are plotted in panel (c) of FIG. 3 as a function of the number of cycles. The color intensity of the liquid droplet inside the microtube including ratchet-like inner wall design a-2 decreased monotonically as the number of activation cycles increased. On the other hand, in the case of the microtube including flat inner wall design a-1, the color intensity remains almost the same throughout the activation cycles. Some fluctuations observed may be attributed to slight differences in data acquiring location and/or disturbances from environmental lights.

The studies of panel (d) of FIG. 3 demonstrate that the rate of mass transport through the microtube including a ratchet-like inner wall design is controllable by control of the duty cycle of activation. The color intensity changes were acquired under activation signals with the period of 1 second and duty cycles at 50%, 37.5%, 25%, and 12.5%, respectively. Using a duty cycle of 50%, mass transport can be completed within 3 cycles of activation, which is suitable for very quick or drastic release. Shorter duty cycles such as 37.5% and 25% required more cycles (19 and 22 cycles, respectively) to complete the mass exchange. The shortest duty cycle of 12.5% required up to 28 cycles to complete mass exchange. The 12.5% duty cycle also demonstrated a steady and uniform release with less fluctuation that other duty cycles, which may be beneficial in the case of continuous release. Furthermore, it is expected that the bubble size (gas volume) (which determines the resonance frequency) will also influence mass transport.

Figure 4:
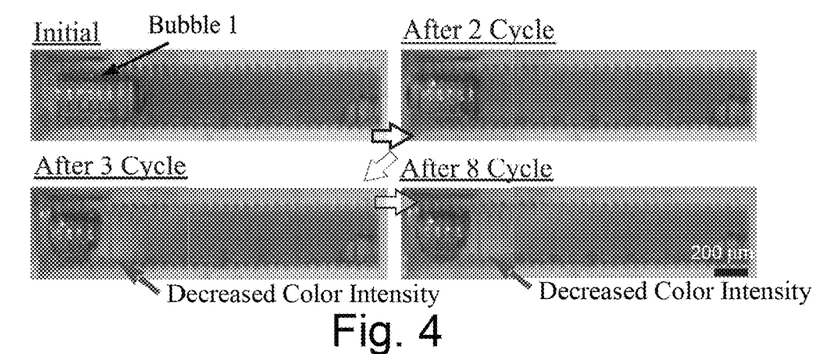
FIG. 4 illustrates studies of the function of a single air/gas volume or air bubble positioned at an open end of a microtube and separating a liquid volume from a surrounding liquid-containing environment, wherein the sequential photographs were taken in an inactivated or initial state (before any activation cycle) and after 2,3,8 cycles of activation, wherein the arrows indicate the portion where mass transport occurred (scale bar=200 µm).

Further studies demonstrated that the presence of rearward, gas bubble 2 is desirable in achieving mass transport bidirectionally between the interior of the microtube and surrounding liquid environment. The functionality of a combination of forward gas bubble 1 and rearward gas bubble 2 was studied via comparison with a microtube in which rearward gas bubble 2 was absent and a dyed water droplet as illustrated in the studies of FIG. 4 as placed adjacent to forward gas bubble 1. That configuration results in a microtube which includes a single gas/air bubble (that is, gas bubble 1 at the open end thereof). The dyed water droplet was positioned rearward of gas bubble 1. However, a tiny air bubble was still trapped at the corner of the sealed end. Because of its size and higher resonance frequency, the tiny air bubble did not generate significant oscillation during activation at 2.4 kHz. When the externally generated acoustic signal was applied, gas bubble 1 oscillated and initiated mass transport from the forward (left) side of the water droplet, close to or in the vicinity of gas bubble 1, which was indicated by the decrease in color intensity in that region (indicated arrows in FIG. 4) after 3 cycles. After more activation cycles, further mass transport/exchange occurred only in the vicinity of gas bubble 1. The color intensity of more rearward regions of the dyed water droplet remained unchanged. Comparing the result of the studies of FIG. 4 with those of FIG. 3, mass exchange in microtubes including the presence of both forward gas bubble 1 and rearward gas bubble 2 occurs completely and throughout the entire droplet, while mass exchange is limited to only the region in the vicinity of forward gas bubble 1 in the absence of rearward gas bubble 2. The results indicate that rearward gas bubble 2 enhances mixing within the liquid droplet while forward gas bubble 1 exchanges mass across forward gas bubble 1 and thereby between the liquid droplet and the surrounding liquid environment.

Figure 5:
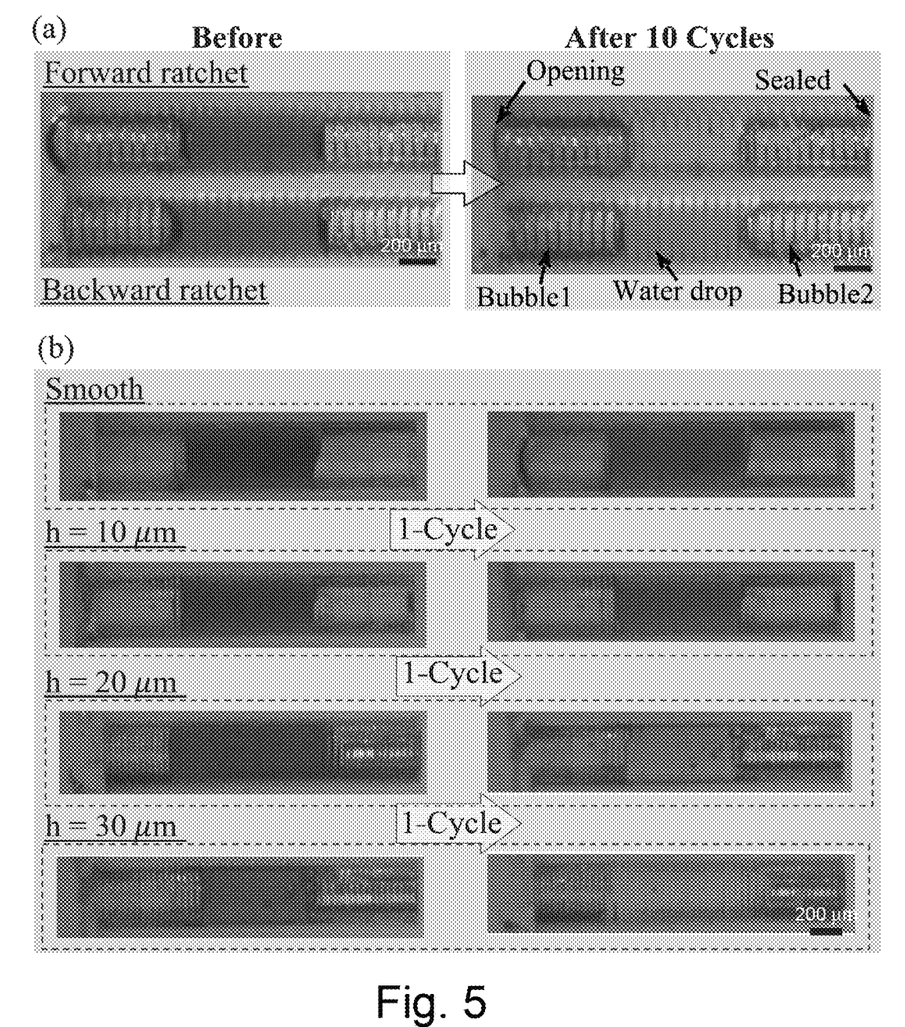
FIG. 5 illustrates the study of the effect of ratchet-like geometry on mass transport wherein panel (a) illustrates a comparison of a forward (inner wall design a-2) and a backward (inner wall design a-3) ratchet-like, inner wall design before and after 10 cycles of activation and panel (b) illustrates a comparison of a flat inner wall design a-1 and a symmetric triangular ratchet-like, inner wall design (at height of 10, 20, and 30 µm; correspond to inner wall designs b-1, b-2, and b-3, respectively) before and after 1 activation cycle, wherein all scale bars represent 200 µm.

Once again, surface texture or roughness, such as a ratchet-like structure, on the interior wall of microtube facilitates mass transport of liquid in a gas bubble: liquid: gas bubble configuration. The effect of ratchet-like geometry was studied by studying various alterations in the ratchet-like structure. First, the direction of ratchet was studied by reversing the leading and receding angle of the ratchet-like structure as backward ratchet interior wall design a-3. The result of mass transport through both forward rachet inner wall design a-2 and backward ratchet inner wall design a-3 is illustrated in panel (a) of FIG. 5. Both ratchet designs can generate mass exchange. However, forward ratchet inner wall design a-2 exhibits a higher exchange rate with less dye left in the droplet after the same excitation/activation cycles. That result indicates that the mass transport phenomenon is favored by a specific direction of the ratchet geometry. However, the directionality of the ratchet geometry will not ultimately prevent mass transport. Furthermore, the effect of cross-sectional area of the ratchet was studied by altering the height of symmetric triangular ratchet inner wall designs b-1, b-2 and b-3 (see panel (b) of FIG. 2). The extent of mass transport occurring within 1 activation cycle (duty cycle=50%) of 4 studied gap heights h (0, 10, 20, 30 μm) are shown in panel*b) of FIG. 5. The results indicated that the deeper gap height h over the range of gap heights studied (which is associated with a larger volume per unit length of the microtube), has greater mass transport rate.

Figure 6:
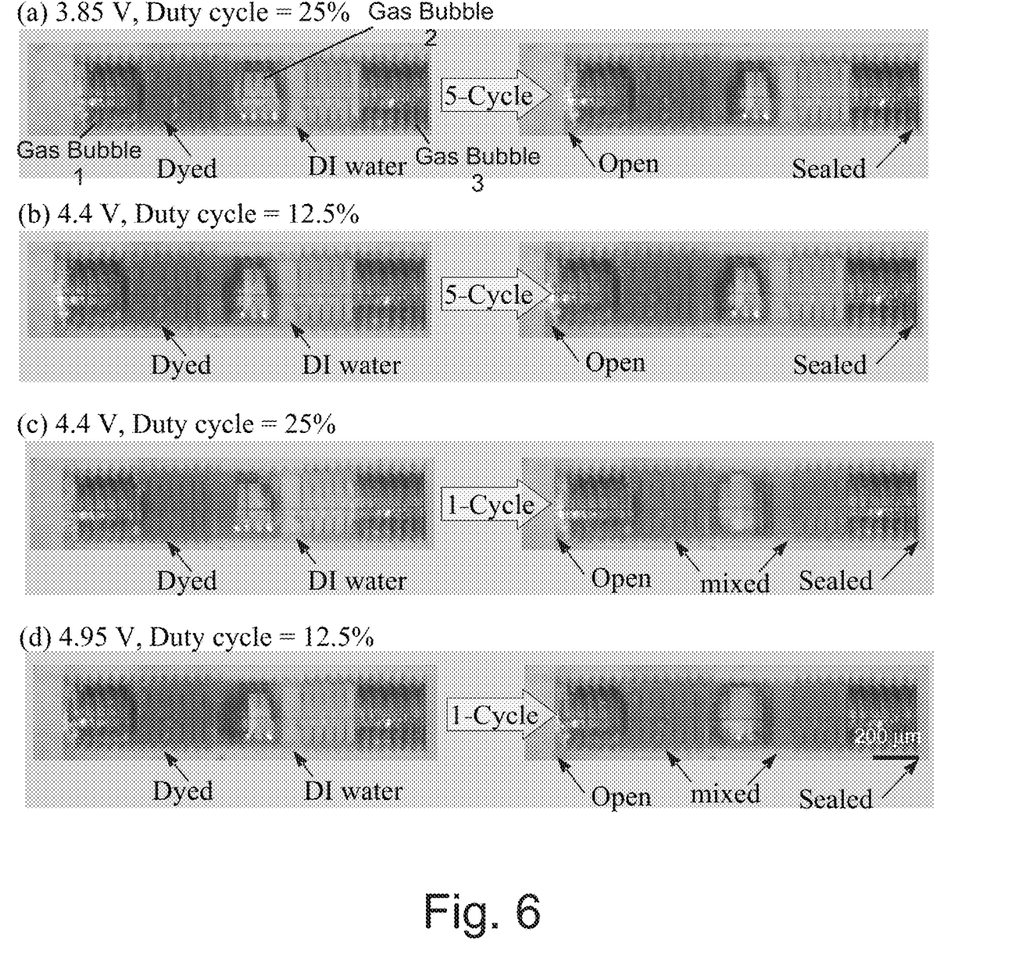
FIG. 6 illustrates studies of embodiments of microtubes hereof having a mixing configuration including two water droplets inside a ratchet-walled microtube which is excited by an externally generate acoustic wave of 2.4 kHz at various voltages and duty cycles, wherein: panel (a) illustrates activation at 3.85 volts and a duty cycle of 25%; panel (b) illustrates activation at 4.4 volts and a duty cycle 12.5%; panel (c) illustrates activation at 4.4 volts and a duty cycle of 25%; and panel (d) illustrates activation at 4.95 volts and a duty cycle of 12.5%, and wherein the scale bar=200 µm.

The results discussed above demonstrate that mass transport occurs across the air/gas bubble positioned at the open end of the microtube. However, further studies indicated that mass transport exists not only between a gas-entrapped liquid droplet within the microtube and surrounding liquid environment, but also may occurs between two liquid droplets entrapped within a microtube wherein a gaseous bubble is positioned therebetween. In a number of studies, two water droplets were placed within a microtube having a ratchet-like inner wall design a-2. One water droplet was dyed blue and the other water droplet was clear or undyed. The system thus included the microtube which included therein (and as described moving from the open end to the sealed end of the microtube) first gas/air bubble 1 adjacent the open end of the microtube, a droplet of dyed water adjacent gas/air bubble 1, a second gas/air bubble 2 adjacent the dyed water droplet, a droplet of deionized or DI water (undyed), and a third gas/air bubble 3 adjacent the sealed end of the microtube as shown in, for example, panel (a) of FIG. 6. Four acoustic signals at 2.4 kHz and different duty cycles were introduced to excite the oscillation of the gas/air bubbles. The acoustic signals were: (1) 3.85 volts, duty cycle=25%, (2) 4.4 volts, duty cycle=12.5%, (3) 4.4 volts, duty cycle=25%, and (4) 4.95 volts, duty cycle=12.5%, and are referenced herein as signal (1) to (4). The results are depicted in panels (a) through (d) of FIG. 6. Signal (1) and (2) had no observable impact on the two droplets. However, signals (3) and (4) resulted in mass exchange between the two liquid droplets. The results indicate that the amplitude of acoustic signal and duty cycle are both important parameters in initiating mass transport. At the smallest amplitude (3.85 volts), mass transport was not activated with duty cycles 12.5% or 25%. A medium level amplitude (4.4 volts) activated mass transport with the longer duty cycle if 25% but not with shorter duty cycle. At the highest amplitude (4.5 volts), mass transport/exchange occurs even at the shorter duty cycle of 12.5%. The results indicate that mass transport through the microtube is activated by any externally generated acoustic wave greater than a threshold amplitude and a threshold duty cycle which may be readily determined. As the amplitude increases, the threshold of duty cycle decreases. The mixing of two droplets in panels (c) and (d) of FIG. 6 were analyzed by color intensity. Before activation, the droplet with dye had the volume concentration of 2.4% v/v and the second droplet had a concentration 0%. If fully mixed, concentrations of two droplets would be the same. The final concentrations were estimated by the length (total volume) and intensity (concentration) of two droplets and were 1.28% v/v and 1.35% v/v in panel (c) and panel (d), respectively. The intensities of the two droplets after mixing were similar, and the final concentrations are 1.33% and 1.38%. It is therefore concluded that the thorough mixing can be accomplished between two droplets without significant leaking to surrounding environment. The minimized leaking to the surrounding liquid may be attributed to the shorter length of the middle bubble than the bubble in the opening. More mass transport occurs to the side of the droplet in the rear end than to the surrounding liquid.

Figure 7A:
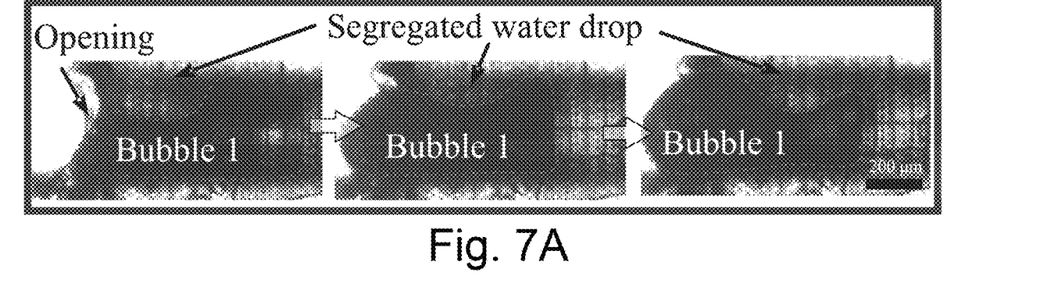
FIG. 7A illustrates sequential, high-speed photographs of a gas bubble (outlined by a dashed or broken line) and a water droplet under high-amplitude oscillation wherein smaller droplets segregate from the liquid droplet and the surrounding water environment.

For the microtubes designs/dimensions studied, it was observed that the stable mass exchange occurred only within a relatively narrow window of frequency range of between 2.4 and 2.5 kHz. Outside of that frequency range, insignificant and/or nonrepeatable mass transport was observed under similar oscillating amplitudes. Increasing the amplitude at other frequencies was observed to sometimes initiates mass transport, but that mass transport was less stable than that which occurs in the above-identified range of frequencies, changed the volume or position of the droplet during mass transport, or even split the bubbles or the droplet, thereby destroying the original configuration. To study the mechanism of acoustic bubble induced mass transport from within the microtubes hereof, the behavior of air/gas bubble 1, which is believed to initiate mass transport between the microtube and the surrounding liquid environment, was observed via a high-speed camera with higher input voltage (2.4 kHz, 7.7 V) to emphasize the motion. During the mass transport, the deformation of air bubble 1 segregates liquid into smaller drops, as illustrated in FIG. 7A. On the other hand, the excitation out of the frequency window identified above results in a mild back and forth movement of the liquid-air interface in the cross-section area only. No segregated droplet passage was observed under the actuation at frequencies outside the frequency window identified above. Suitable or optimal operating conditions for a particular system hereof are readily determinable via well-known engineering principles and studies as described herein.

Figure 7B:
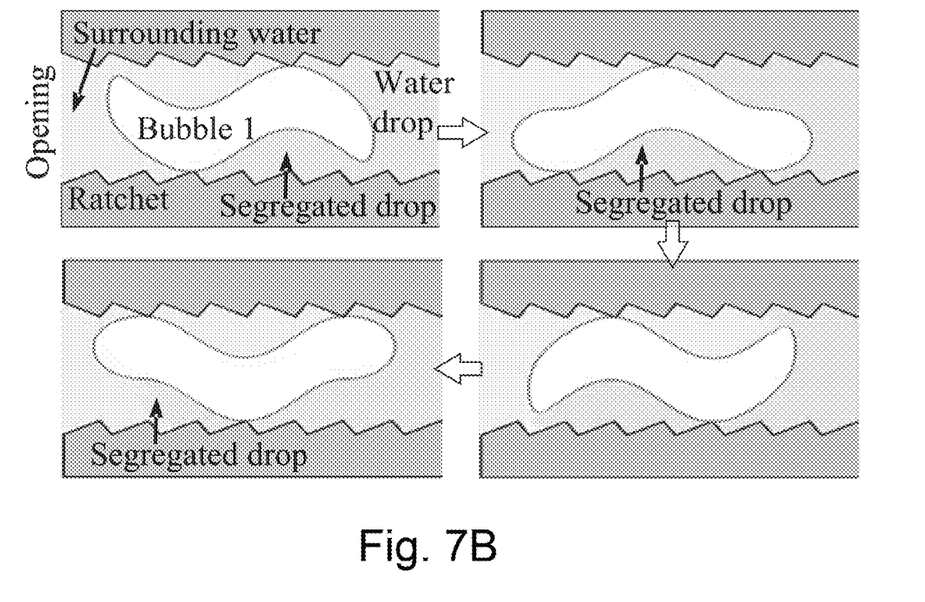
FIG. 7B illustrates simplified or idealized schematic sketches of the sequential high-speed images of FIG. 7A, which clarify a proposed mechanism of mass transport.

The idealized schematic illustrations of FIG. 7B illustrate a proposed mechanism of how the liquid is transported via the oscillation of the bubble in FIG. 7B. Without limitation to any mechanism, liquid from the entrapped liquid droplet is stretched and segregated by the deformation of oscillating gas bubble 1, eventually forming smaller droplets between the ratchet surface and gas bubble 1. Subsequently, the undulating motion of oscillating gas bubble 1 transports the smaller droplets out of the microtube. Liquid from the surrounding liquid environment is also separated into smaller drops and transported into the microtube generally contemporaneously. Thus, bubble oscillation with large amplitude stretches and segregates the liquid droplet into smaller droplets, and the undulating motion of the bubble transports the segregated droplets on the ratchet-like surface. All these processes occur in both directions (from the liquid droplet within the microtube to the surrounding liquid environment (water) and vice versa).

Figure 7C:
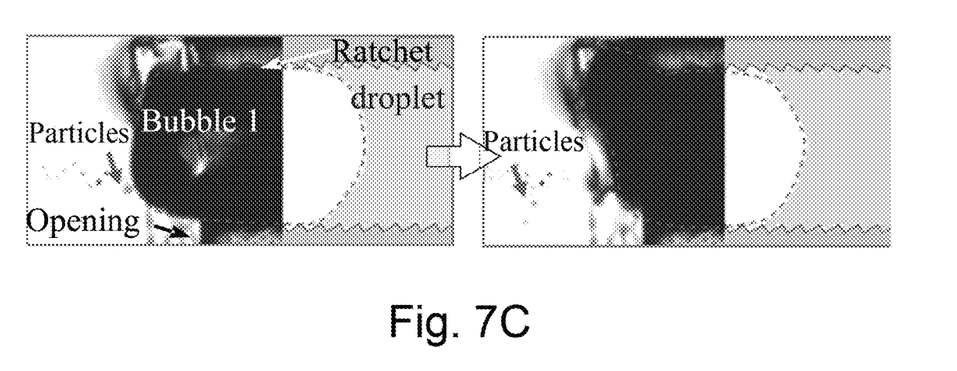
FIG. 7C illustrates high-speed photographic images near the microtube opening, wherein microparticles initially seeded in the water droplet are ejected out of the tube (see arrows) when the gas bubble (outlined by a dashed or broken line) oscillates.

To confirm the motion of the segregated, smaller droplet, 20 μm plastic particles were seeded into the entrapped droplet. FIG. 7C shows that the particles are ejected out of the microtube opening as soon as the oscillation begins, which demonstrates that the constituents of the droplet entrapped within the microtube is delivered from the microtube to surrounding liquid environment.

Mass transport of liquid at a microscale via the devices, systems and methods hereof can thus be remotely activated and precisely controlled by, for example, an external acoustic wave signal to excite oscillation of gaseous bubble within the microtube. A basic configuration of a system hereof includes a liquid droplet positioned between two gaseous bubbles within a microtube including an open end and a closed or sealed end. The microtube may include a textured or rough inner wall (for example, including a ratchet-like inner or interior wall). When the forward gas bubble (adjacent the open end) is oscillating, it transports the liquid from the liquid droplet within the microtube to the surrounding liquid environment. The rearward bubble (adjacent or closer to the closed or sealed end) enables thorough mixing over the intermediate liquid droplet to achieve effective mass transport. Efficient mass transport may by achieved via predeterminable specific oscillation modes of the outer bubble, which can be selectively activated by control (for example, frequency) of acoustic input. The rate of release (mass transport) can be tuned through control of the duty cycle of activation, and the total amount of mass released can be controlled by the number of activation cycles. Control of the energy input to an implanted system hereof enables either a pulsatile or a continuous mass release profile with on-demand control for different types of therapeutic or diagnostic procedures. Moreover, mass transport can be achieved between two liquid droplets inside the microtube and separated by a gas bubble, which provides options for complex manipulation of a plurality of liquid droplets within the microtube.

Experimental Examples

Fabrication. Microtubes including a ratchet-like textured inner wall were fabricated via a 3D laser printer utilizing two-photon polymerization (Nanoscribe GmbH, of Eggenstein-Leopoldshafen, Baden-Wurttemberg, Germany). First, a drop of photoresist (IP-S) was placed on an ITO-coated substrate and cured into the designed structure by the focused laser beam. Second, excess photoresist was removed by SU8-developer (MicroChem Corp., of Westborough, Massachusetts USA), followed by a rinse of isopropanol (Sigma-Aldrich of St. Louis, Missouri USA). Finally, the microtube was completely dried and coated with 2% Teflon on its inner or interior wall.

System setup. The configuration of the microtube is shown in FIGS. 1A through 1C. A 0.1-μL blue-dyed water droplet (concentration=2.4% v/v) was first injected to the middle of the microtube by a microliter syringe (Hamilton Company of Reno, Nevada USA) to form a liquid drop that fully blocks the cross-section of the microtube. A volume of gas or gaseous bubble is simultaneously entrapped adjacent the sealed end of the microtube (gas bubble 2). Subsequently, by submerging the microtube into the tank filled with DI water, another gas bubble (gas bubble 1) is automatically entrapped in the open side of the microtube as a result of the hydrophobicity of the inner wall of the microtube. As a result, the droplet is positioned/trapped between the two bubbles in the microtube. The two bubbles were acoustically excited by a piezo disk glued to the wall of testing water tank.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system, comprising:
   a delivery system comprising
      a tube comprising a first open end and a second closed end, the inner wall of the tube exhibiting surface roughness,
      a first liquid volume comprising a first liquid within the tube, and
      a first gas volume within the tube adjacent the first open end and separating the first liquid volume from a surrounding environment of the tube, and
   a drive, remote from the delivery system, to transmit acoustic or pressure waves to controllably oscillate the first gas volume.

2. The system of claim 1 wherein the delivery system is an implantable system and the drive is ex vivo.

3. The system of claim 2 wherein the drive is configured to transmit the acoustic or pressure waves to controllably oscillate the first gas volume so that mass is transferred across a length of the tube occupied by the first gas volume from the first liquid volume to the surrounding environment during oscillation of the first gas volume.

4. The system of claim 3 wherein the inner wall of the tube is hydrophobic.

5. The system of claim 3 wherein the tube comprises a plurality of axially spaced flanges extending radially inward.

6. The system of claim 5 wherein the plurality of axially spaced flanges forms a ratchet-like surface.

7. The system of claim 3 wherein the delivery system further comprises a second gas volume positioned within the tube so that the first liquid volume is positioned between the first gas volume and the second gas volume, the acoustic or pressure waves further being configured to controllably oscillate the second gas volume.

8. The system of claim 7 wherein the delivery system further comprises at least a second liquid volume comprising a second liquid within the tube adjacent the second gas volume on a side thereof opposite to a side adjacent the first liquid volume and a third gas volume adjacent the second liquid volume on a side thereof opposite the side adjacent the second gas volume, the acoustic or pressure waves further being configured to controllably oscillate the second gas volume.

9. The system of claim 8 wherein the composition of the second liquid volume is different from the composition of the first liquid volume.

10. The system of claim 7 wherein the drive is controlled to control the acoustic or pressure waves to be within a determined range of amplitude and a determined range of frequency.

11. The system of claim 7 wherein a duty cycle of the drive is controlled to control oscillation of the first gas volume and the second gas volume.

12. The system of claim 7 wherein the drive comprises a piezo actuator or a pressure wave generator.

13. The system of claim 7 wherein the tube has an average inner diameter no greater than 3 cm.

14. The system of claim 7 wherein the tube has a length in the range of 10 μm to 3 cm.

15. The system of claim 7 wherein the tube has an average inner diameter no greater than 500 μm.

16. The system of claim 7 wherein the tube has a length in the range of 10 μm to 100 μm.

17. A method of mass exchange between a delivery system and an environment comprising liquid, comprising:
   placing the delivery system in the environment, the delivery system comprising
      a tube comprising a first open end and a second closed end, an inner wall of the tube having surface roughness,
      a first liquid volume comprising a first liquid within the tube, and a first gas volume within the tube adjacent the first open end and separating the first liquid volume from the environment surrounding the tube, and
   transmitting acoustic or pressure waves from a drive positioned at a position remote from the delivery system to controllably oscillate the first gas volume.

18. The method of claim 15 wherein the environment is an in vivo environment, the delivery system is an implantable system, the liquid in the environment is a bodily fluid, and the position remote from the delivery system is ex vivo.

19. The method of claim 18 wherein the drive transmits the acoustic or pressure waves to controllably oscillate the first gas volume so that mass is transferred across a length of the tube occupied by the first gas volume from the first liquid volume to the surrounding environment during oscillation of the first gas volume.

20. The method of claim 19 wherein the inner wall of the tube is hydrophobic.

21. The method of claim 19 wherein the tube comprises a plurality of axially spaced flanges extending radially inward.

22. The method of claim 21 wherein the plurality of axially spaced flanges forms a ratchet-like surface.

23. The method of claim 19 wherein the delivery system further comprises a second gas volume positioned within the tube so that the first liquid volume is positioned between the first gas volume and the second gas volume, the acoustic or pressure waves further being configured to controllably oscillate the second gas volume.

24. The method of claim 23 wherein the delivery system further comprises at least a second liquid volume comprising a second liquid within the tube adjacent the second gas volume on a side thereof opposite to a side adjacent the first liquid volume and a third gas volume adjacent the second liquid volume on a side thereof opposite the side adjacent the second gas volume, the acoustic or pressure waves further being configured to controllably oscillate the second gas volume.

25. The method of claim 24 wherein the composition of the second liquid volume is different from the composition of the first liquid volume.

26. The method of claim 23 further comprising controlling the acoustic or pressure waves to be within a determined range of amplitude and a determined range of frequency.

* * * * *

UNITED STATES PATENT AND TRADEMARK OFFICE
CERTIFICATE OF CORRECTION

| | | |
|---|---|---|
| PATENT NO. | : 11,975,171 B2 | Page 1 of 1 |
| APPLICATION NO. | : 17/151173 | |
| DATED | : May 7, 2024 | |
| INVENTOR(S) | : Sung Kwon Cho and Fang-Wei Liu | |

It is certified that error appears in the above-identified patent and that said Letters Patent is hereby corrected as shown below:

In the Claims

Column 16, Line 38, Claim 18 delete "The method of claim 15" and insert --The method of claim 17--.

Signed and Sealed this
First Day of October, 2024

Katherine Kelly Vidal
*Director of the United States Patent and Trademark Office*